(12) United States Patent
Ochi et al.

(10) Patent No.: US 7,314,719 B2
(45) Date of Patent: Jan. 1, 2008

(54) METHOD FOR INCREASING PRODUCTIVITY OF SECONDARY METABOLITE BY CONFERRING DRUG-RESISTANT MUTATIONS

(75) Inventors: Kozo Ochi, 5-73, Ninomiya 4-chome, Tsukuba-shi, Ibaraki (JP) 305-0051; Haifeng Hu, Shanghai (CN); Motohiro Hino, Osaka (JP); Akihiko Fujie, Osaka (JP); Hideyuki Muramatsu, Osaka (JP)

(73) Assignees: The National Food Research Institute, Tsukuba-shi (JP); Kozo Ochi, Tsukuba-shi (JP); Astellas Pharma Inc., Tokyo (JP)

( * ) Notice: Subject to any disclaimer, the term of this patent is extended or adjusted under 35 U.S.C. 154(b) by 237 days.

(21) Appl. No.: 10/473,364

(22) PCT Filed: Mar. 29, 2002

(86) PCT No.: PCT/JP02/03161

§ 371 (c)(1),
(2), (4) Date: Sep. 30, 2003

(87) PCT Pub. No.: WO02/079453

PCT Pub. Date: Oct. 10, 2002

(65) Prior Publication Data

US 2004/0175778 A1    Sep. 9, 2004

Related U.S. Application Data

(60) Provisional application No. 60/279,665, filed on Mar. 30, 2001.

(51) Int. Cl.
*G01N 33/35* (2006.01)
*C12P 21/06* (2006.01)

(52) U.S. Cl. ..................... 435/7.1; 435/69.1
(58) Field of Classification Search ............... 435/245, 435/252.1, 253.5
See application file for complete search history.

(56) References Cited

U.S. PATENT DOCUMENTS 4,680,260 A * 7/1987 Debabov et al. .......... 435/69.51
5,310,677 A * 5/1994 Pollock et al. ............ 435/252.1
5,837,458 A * 11/1998 Minshull et al. ............... 435/6

FOREIGN PATENT DOCUMENTS

GB    2 103 617    2/1983

OTHER PUBLICATIONS

Yoshiko Hosoya et al. Antimicrobial Agents and Chemotherapy. 1998, vol. 42, No. 8, pp. 2041-2047.*
J. Shima et al.: "Induction of actinorhodin production by rpsL (encoding ribosomal protein S12) mutations that confer streptomycin resistance in *Streptomyces lividans* and *Streptomyces coelicolor* A3(2)" Journal of Bacteriology, vol. 178, No. 2, pp. 7276-7284, Dec. 1996.
A. Hesketh et al.: "A novel method for improving *Streptomyces coelicolor* A3(2) for production of actinorhodin by introduction of rpsL (encoding ribosomal protein S12) mutations conferring resistance to streptomycin" The Journal of Antibiotics, vol. 50, No. 6, pp. 532-535, Jun. 1997.
Kozo Ochi et al.: "Genetic mapping and characterization of novel mutations which suppress the effect of a relC mutation on antibiotic production in *Streptomyces coelicolor* A3(2)" Journal of Antibiotics (Tokyo), vol. 51, No. 6, pp. 592-595, Jun. 1998.
J. Stastna et al.: "An antibiotic-overproducing mutant of *Streptomyces granaticolor* with impaired differentiation" Journal of Basic Microbilogy, vol. 27, No. 9, pp. 521-528, 1987.
Yoshiko Okamoto-Hosoya et al.: "Resistance to paromomycin is conferred by rpsL mutations, accompanied by an enhanced antibiotic production in *Streptomyces coelicolor* A3(2)" Journal of Antibiotics, vol. 53, No. 12, pp. 1424-1427, Dec. 2000.
H. Hu et al.: "Novel approach for improving the productivity of antibiotic-producing strains by inducing combined resistant mutations" Applied and Environmental Microbiology, vol. 67, No. 4, pp. 1885-1892, Apr. 2001.
Annu. Rev. Microbio., vol. 53, pp. 411-446 1999, Bentley et al.
Practical *Streptomyces* Genetics, pp. 10-11 2000.
Actinomycetologica, vol. 5, pp. 86-99, (1991), Ikeda et al.
Protein, Nucleic Acid, Enzyme, vol. 44, No. 13, pp. 1967-1974 1999, (in Japanese).
Kagaku To Seibutsu, vol. 37, No. 11, pp. 731-737 1999, (in Japanese).
Y. Manjula Rao, et al., "Direct biosynthesis of ascorbic acid from glucose by *Xanthomonas campestris* through induced free-radicals", Biotechnology Letters, vol. 22, 2000, pp. 407-411.

* cited by examiner

*Primary Examiner*—Robert B. Mondesi
(74) *Attorney, Agent, or Firm*—Oblon, Spivak, McClelland, Maier & Neustadt, P.C.

(57) ABSTRACT

This invention relates to a method for increasing the productivity of the secondary metabolite in a micro-organism, for example, the improvement of antibiotic producers by conferring drug-resistant mutations to micro-organisms.

17 Claims, 10 Drawing Sheets

FIG. 10
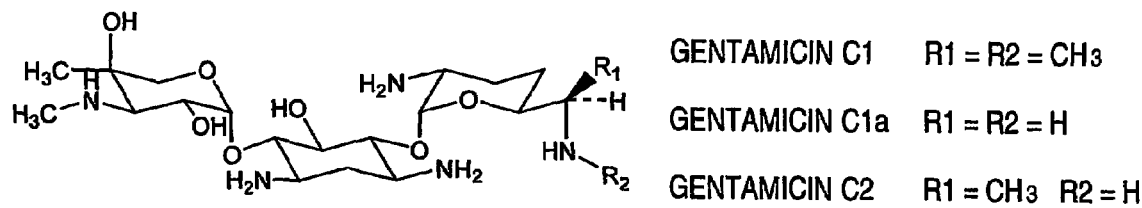
GENTAMICIN C1   R1 = R2 = CH3
GENTAMICIN C1a  R1 = R2 = H
GENTAMICIN C2   R1 = CH3  R2 = H
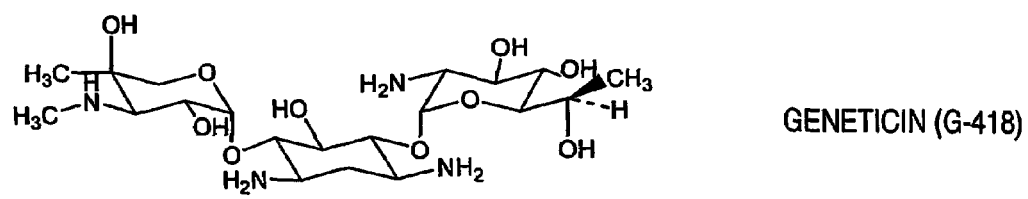
GENETICIN (G-418)
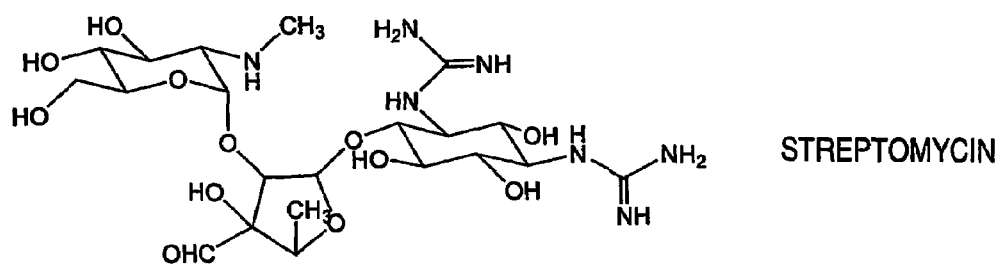
STREPTOMYCIN
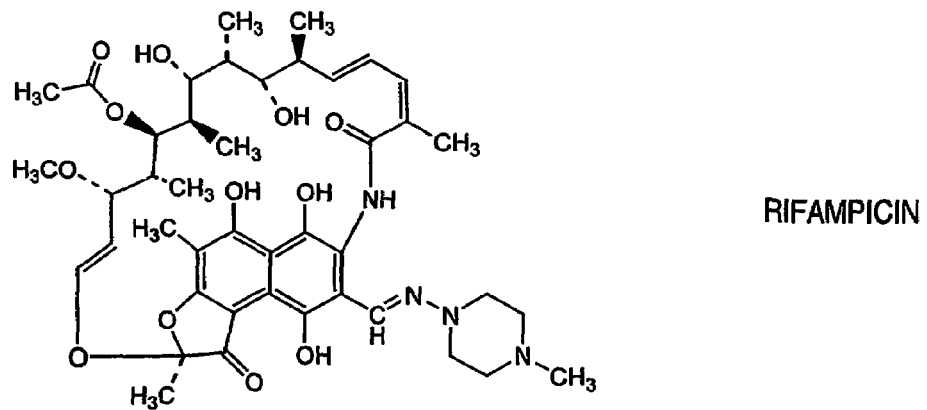
RIFAMPICIN

SEQUENCE LISTING

```
<160> NUMBER OF SEQ ID NOS: 5

<210> SEQ ID NO 1
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 1
attcggcaca cagaaac                                                   17

<210> SEQ ID NO 2
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 2
agaggagaac cgtagac                                                   17

<210> SEQ ID NO 3
<211> LENGTH: 24
<212> TYPE: DNA
<213> ORGANISM: Artificial Sequence
<220> FEATURE:
```

```
<223> OTHER INFORMATION: synthetic oligonucleotide

<400> SEQUENCE: 3
ggccgctaca aggtgaacaa gaag                                                24

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
cgatgacgaa gcggtcctcc                                                     20

<210> SEQ ID NO 5
<211> LENGTH: 65
<212> TYPE: PRT
<213> ORGANISM: Streptomyces coelicolor

<400> SEQUENCE: 5

Gln Leu Ser Gln Phe Met Asp Gln Asn Asn Pro Leu Ser Gly Leu Thr
1               5                   10                  15

His Lys Arg Arg Leu Asn Ala Leu Gly Pro Gly Gly Leu Ser Arg Glu
            20                  25                  30

Arg Ala Gly Phe Glu Val Arg Asp Val His Pro Ser His Tyr Gly Arg
        35                  40                  45

Met Cys Pro Ile Glu Thr Pro Glu Gly Pro Asn Ile Gly Leu Ile Gly
    50                  55                  60

Ser
65
```

METHOD FOR INCREASING PRODUCTIVITY OF SECONDARY METABOLITE BY CONFERRING DRUG-RESISTANT MUTATIONS

This application is a 371, National Stage, of PCT/JP02/03161 filed on Mar. 29, 2002 which claims benefit of 60/279,665 filed on Mar. 30, 2001.

TECHNICAL FIELD

This invention relates to a method for increasing the productivity of the secondary metabolite such as antibiotics in a microorganism by conferring a drug-resistance to the microorganism. More particularly, the present invention relates to the improvement of the secondary metabolite by conferring combined drug-resistant mutations to microorganisms.

TECHNICAL BACKGROUND

"Secondary metabolites" was originally used by plant physiologists to classify botanicals (e.g. dyes, fragrances, and medicinals) with no obvious function in the plants that produced them. It now encompasses a heterogous group of compounds, usually of low relative molecular mass, and made mostly but not exclusively by organisms without a nervous system (i.e., bacteria, fungi, and plants). The notion of secondary metabolism was embrassed by microbiologists in the 1960s, with attention focusing on antibiotics and other bioactive microbial products (Bently, R. et al, *Annu. Rev. Microbio.* (1999) 53: 411-446).

It is well known that members of the genus *Streptomyces* produce a great many antibiotics and other classes of biologically active secondary metabolites. The genus *Streptomyces* belongs to the order Actinomycetales. In general, the order Actinomycetales means Actinomycetes. Actinomycetes make over 60% of the known secondary metabolites that are produced by microorganisms, and amongst them nearly 80% are made by members of the genus *Streptomyces*, with other genera trailing numerically (Kieser, T. et al, *Practical Streptomyces Genetics* (2000): 10-11).

Most antibiotics applied in clinical were first isolated from the metabolites of microbes including bacteria, fungi and actinomycetes, in which *Streptomyces* are known to be the most effective producers. Genetic recombination and manipulation in *Streptomyces* have been established by D. A. Hopwood and his co-workers (Hopwood et al. *Genetic manipulation of Streptomyces*, a laboratory manual, 1985). So far, treatment with mutagens and the screening of resultant clones has been repeated and adopted as a procedure for the improvement of antibiotic-producing *Streptomyces* and produced good results. However, this method has some disadvantageous properties such as labor-consuming, time-consuming, costly, non-reproductive and low frequency etc. The current intentional methods for improving strains are genetic recombination and manipulation that represent an important technique in strain improvement such as protoplast fusion, structural gene amplification, regulatory genes and resistance genes cloning etc. (Ikeda et al. *Actinomycetologica* 1991, 5:86-99). Obviously, these methods require a better knowledge about biochemistry and genetics of antibiotic production.

As described above, some methods for improving strains have been invented and applied in fermentation industry. It is known that a productivity of actinorhodin in *Streptomyces coelicolor* can be improved by conferring streptomycin resistance to it (*Protein, Nucleic Acid, Enzyme*, vol. 44, No. 13, p 1967-1974 (1999); *Kagaku to Seibutsu*, vol. 37, No. 11, p 731-737 (1999)). However, no report has ever been made concerning more effective methods to increase the productivity of the secondary metabolites.

An object of the present invention is to provide a method for increasing the productivity of the secondary metabolite by a microorganism in a labor-saving, time-saving, high efficient and semi-rational way and being applicable for the strains without more knowledge of, for example, antibiotic biochemistry and genetics.

DISCLOSURE OF THE INVENTION

In order to accomplish the object as described above, the inventors made extensive studies and found the following unexpected new findings. That is, the actinorhodin productivity in *Streptomyces coelicolor* can be improved by conferring a resistance against two or more antibiotics, such as: streptomycin, geneticin, gentamicin and rifampicin. Each antibiotic possesses the ability to increase the productivity by inducing the respective mutations. Using one streptomycin-resistant mutant as starting strain, the productivity of actinorhodin could be further increased by introducing another antibiotic-resistant mutation such as: geneticin-resistant, gentamicin-resistant or rifampicin-resistant mutation, which means that double mutations (streptomycin and geneticin, streptomycin and gentamicin, streptomycin and rifampicin combined resistant mutations) could continuously increase productivity of actinorhodin. Finally, by introducing rifampicin-resistant mutation into the double (streptomycin and gentamicin) mutants, the productivity could be increased further. It was confirmed that by introducing combined three antibiotic resistant mutations, the productivity of actinorhodin in *Streptomyces coelicolor* could continuously increase in a stepwise way and reach a high producing level.

The present invention was accomplished based on the new findings described above.

Thus, the present invention provides:

(1) A method for increasing a productivity of a secondary metabolite in a microorganism by conferring a resistance against two or more antibiotics to said microorganism.

(2) A method for obtaining a microorganism having an increased productivity of a secondary metabolite, which comprises the steps of conferring a resistance against two or more antibiotics to said microorganism by culturing it in a medium containing the antibiotics, wherein the concentration of said antibiotics is higher than MIC of said antibiotics against the original microorganism, and isolating colonies which can grow in the medium.

(3) The method as described in (1) or (2) above, wherein said microorganism is a bacterium.

(4) The method as described in (1) or (2) above, wherein said microorganism belongs to the genus selected from the group consisting of *Streptomyces*, genus *Bacillus*, and genus *Pseudomonas*.

(5) The method as described in (1) or (2) above, wherein said microorganism is selected from the group consisting of *Streptomyces coelicolor, Streptomyces lividans, Streptomyces antibioticus, Streptomyces chattanoogensis, Bacillus subtilis, Bacillus cereus*, and *Pseudomonas pyrrocinia*.

(6) The method as described in (1) or (2) above, wherein said antibiotic is selected from the group consisting of ribosomal protein-attacking antibiotics, ribosomal RNA-attacking antibiotics, and RNA polymerase-attacking antibiotics.

(7) The method as described in (1) or (2) above, wherein said antibiotic is selected from the group consisting of streptomycin, geneticin, gentamicin, and rifampicin.

(8) The method as described in (1) or (2) above, wherein said secondary metabolite is selected from the group consisting of antibiotics, enzymes and physiologically active substances.

(9) A method for producing a secondary metabolite, which comprises the steps of culturing in a medium a microorganism having a resistance against at least two antibiotics and having an increased productivity of the secondary metabolite in comparison to the original microorganism thereof, forming and accumulating a secondary metabolite, and recovering the secondary metabolite therefrom.

(10) The method as described in (9) above, wherein said microorganism is a bacterium.

(11) The method as described in (9) above, wherein said microorganism belongs to the genus selected from the group consisting of Streptomyces, genus Bacillus, and genus Pseudomonas.

(12) The method as described in (9) above, wherein said microorganism is selected from the group consisting of Streptomyces coelicolor, Streptomyces lividans, Streptomyces antibioticus, Streptomyces chattanoogensis, Bacillus subtilis, Bacillus cereus, and Pseudomonas pyrrocinia.

(13) The method as described in (9) above, wherein said antibiotic is selected from the group consisting of ribosomal protein-attacking antibiotic, ribosomal RNA-attacking antibiotics, and RNA polymerase-attacking antibiotics.

(14) The method as described in (9) above, wherein said antibiotic is selected from the group consisting of streptomycin, geneticin, gentamicin, and rifampicin.

(15) The method as described in (9) above, wherein said secondary metabolite is selected from the group consisting of antibiotics, enzymes and physiologically active substances.

(16) A microorganism having an increased productivity of the secondary metabolite in comparison to an original strain thereof, which is produced in accordance with the method of (1) or (2) above.

(17) The microorganism as described in (16) above, wherein said microorganism is a bacterium.

(18) The microorganism as described in (16) above, wherein said microorganism belongs to the genus selected from the group consisting of Streptomyces, genus Bacillus, and genus Pseudomonas.

(19) The microorganism as described in (16) above, wherein said microorganism is selected from the group consisting of Streptomyces coelicolor, Streptomyces lividans, Streptomyces antibioticus, Streptomyces chattanoogensis, Bacillus subtilis, Bacillus cereus, and Pseudomonas pyrrocinia.

(20) A method for increasing a productivity of a secondary metabolite in a microorganism by conferring a resistance against a single antibiotic, excepting streptomycin, to said microorganism.

As another aspect of the invention, a method is provided for inducing other antibiotic biosynthesis in microorganisms by introducing a single or multi drug-resistant mutation and providing a new approach to find new antibiotics.

BRIEF DESCRIPTION OF THE DRAWINGS

This invention is illustrated by reference to the following drawings:

FIG. 10 is a graph indicating the structures of four antibiotics used for conferring the resistance, including gentamicin, geneticin, streptomycin and rifampicin.

BEST MODE FOR CARRYING OUT THE INVENTION

Figure 1:
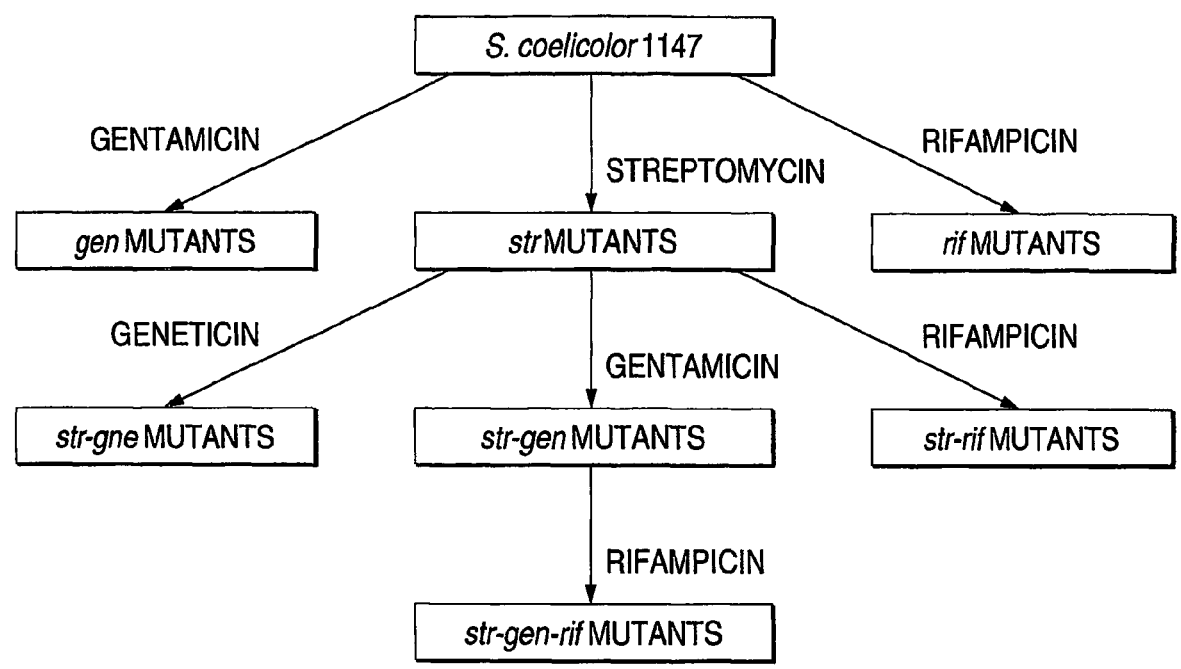
FIG. 1 is the graph indicating the strategy for constructing combined drug-resistant mutants. Three kinds of single mutants and double mutants and one kind of triple mutants were constructed as shown.
Figure 2:
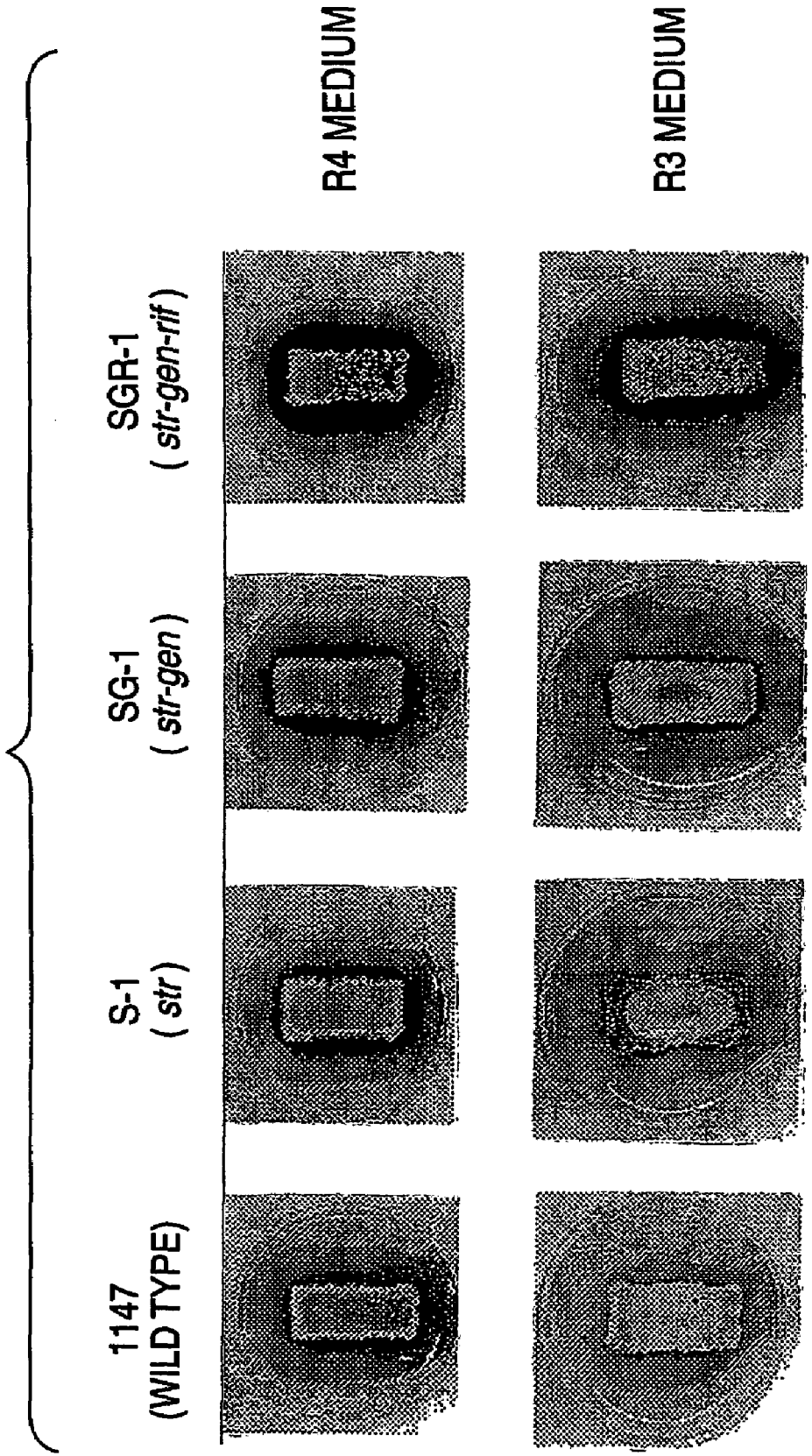
FIG. 2 is a photograph indicating the ability to produce aerial mycelia and actinorhodin in Streptomyces coelicolor wild type and mutant strains. Spores were inoculated on R4 and R3 agar plates, and incubated at 30° C. for 6 days.
Figure 3:
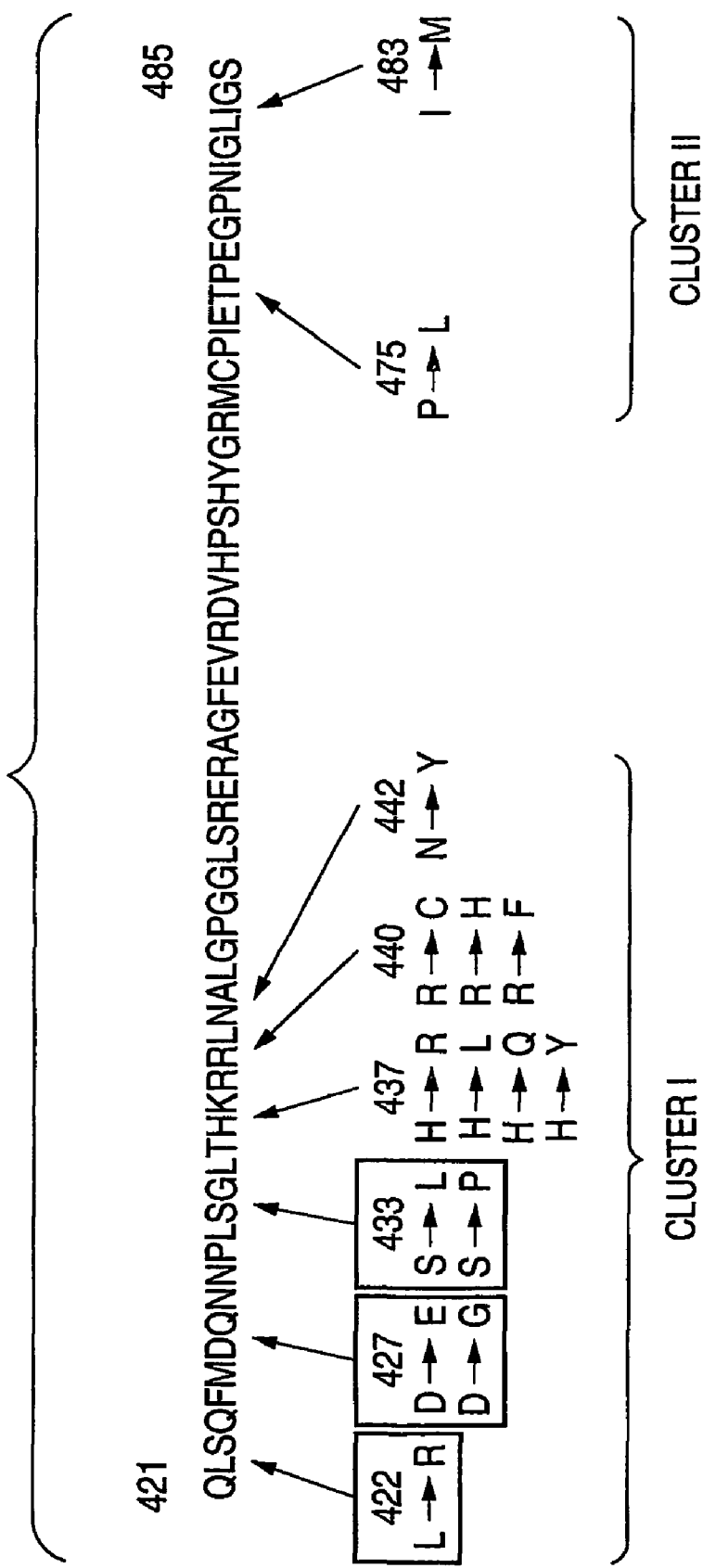
FIG. 3 is a graph indicating amino acid alterations in the β-subunits of RNA polymerases (SEQ ID NO:5) in rifampicin-resistant mutants. Clusters I and II represent the previously known resistance-determining regions. Numbering originates from the starting amino acid (Met) of the open reading frame. Mutation positions are indicated by arrows and numbers, and single capital letters denote the altered amino acids found in this study. Shaded parts indicate the substitutions newly found in our study.
Figure 4:
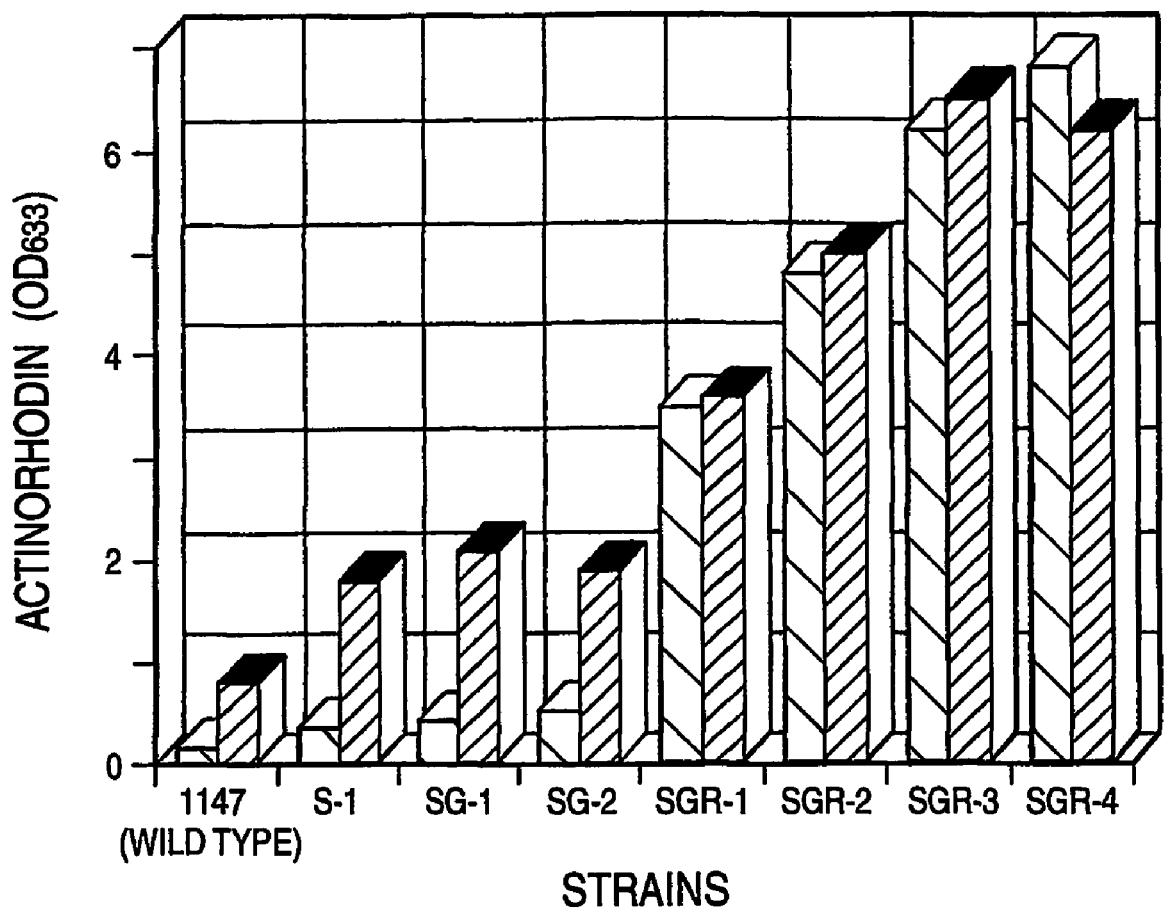
FIG. 4 is a graph indicating comparison of actinorhodin production between media R3 (□) and R4 (■). Actinorhodin was determined after 6 days of incubation.

The microorganism used in the present invention is not particularly limited as long as the productivity of the secondary metabolite thereof can be increased by making the microorganism to be resistant to two or more antibiotics. It is preferable to use soil microorganism that produce agriculturally and/or medically useful antibiotics, enzymes and biologically active substances. Preferable one is bacteria. More preferable one is Actinomycetes. Examples of those belonging to Actinomycetes may be exemplified as genus Streptomyces, genus Bacillus, genus Pseudomonas, etc. And the most preferable one is genus Streptomyces. Specific non-limiting illustrative examples of the bacteria include Streptomyces coelicolor, Streptomyces lividans, Streptomyces antibioticus, Streptomyces chattanoogensis, Bacillus subtilis, Bacillus cereus, and Pseudomonas pyrrocinia.

The microorganism can be isolated from the nature by the known method or available from the culture collections such as ATCC. The microorganism may be any of wild strains, mutant strains, cell fusion strains, transduced strains or recombinant strains constructed by means of recombinant DNA techniques, and may be any ones which have already been used in a fermentation industry as producers for agriculturally and/or medically used antibiotics, enzymes, biologically active substances.

The secondary metabolite is not particularly limited as long as the productivity thereof can be increased by making the microorganism to be resistant to one or more antibiotics. Preferable secondary metabolites include agriculturally and/or medically useful antibiotics (for example: actinomycin from *Streptomyces antibioticus* 3720, fredericamycin from *Streptomyces chattanoogensis* ISP5002, FR900493 from *Bacillus cereus* 2045, and pyrrolnitrin from *Pseudomonas pyrrocinia* 2327, etc.), enzymes (for example: protease from *Bacillus* sp., amylase from *Bacillus* sp., acylase from *Streptomyces lavendulae*, adenosine deaminase from *Micrococcus flavus*, and demethylase from *Streptomyces punipalus*, etc.), and biologically active substances (for example: FK506 from *Streptomyces tsukubaensis*, WS7739 from *Streptomyces phaeofaciens* No.7739, and WS1279 from *Streptomyces willmorei* No.1279, etc.).

The antibiotic used in the present invention to introduce an mutation to the microorganism is not particularly limited as long as the microorganism which is conferred resistant to the antibiotic can produce the secondary metabolite. The preferable antibiotic include those called ribosome-attacking antibiotics including ribosomal protein-attacking antibiotics (e.g., ribosomal S12 protein-attacking antibiotics) and ribosomal RNA-attacking antibiotics, and RNA polymerase-attacking antibiotics.

In order to increase a productivity of a secondary metabolite in a microorganism, it is preferable to confer a resistance against two or more antibiotics to a microorganism. Particularly, a resistance against two or three antibiotics to a microorganism is more preferable. And the most preferable one is a resistance against three antibiotics to a microorganism.

Preferable combination of antibiotics for conferring resistance is (1) two different aminoglycoside antibiotics, (2) one aminoglycoside antibiotic and one ansamycin antibiotic, and (3) two different aminoglycoside antibiotics and one ansamycin antibiotic.

Specific non-limiting examples of the antibiotic include aminoglycoside class antibiotics such as streptomycin, geneticin and gentamicin and ansamycin class antibiotics such as rifampicin.

The method for obtaining the antibiotic-resistant mutant microorganism from the original microorganism is not particularly limited. Preferably, an original microorganism is cultured in a medium containing the antibiotic and the antibiotic-resistant spontaneous mutants may be obtained by isolating colonies which can grow on the antibiotic. Alternatively, a microorganism may be subjected to the usual mutation treatment, such as ultraviolet ray irradiation or chemical treatment with N-methyl-N'-nitro-N-nitrosoguanidine (NTG) or nitrous acid, and antibiotic-resistant mutants may be obtained by isolating colonies which can grow on the antibiotic. In this step, the concentration of the antibiotic in a medium is preferably controlled to become higher than MIC for the original microorganism.

Preferably, the concentration of antibiotics is two times or more, more preferably 5 times or more, most preferably 10 times or more, higher than MIC (Minimum Inhibitory Concentration) of the original microorganism. For example, in case that streptomycin is adopted as the antibiotic, the preferable concentration thereof is 5- to 100-times higher than MIC against the original microorganism. And in case that rifampicin is adopted as the antibiotic, the preferable concentration thereof is 5- to 40-times higher than MIC against the original microorganism. And in case that gentamicin is adopted as the antibiotic, the preferable concentration thereof is 2-times higher than MIC against the original microorganism.

This step may be further repeated to obtain a multi (two or more)-resistant microorganism which is resistant to two or more antibiotics.

Then, a mutant which can produce the intended secondary metabolite in an increased amount is selected by an appropriate way. For example, it may be selected by analytical method (e.g., TLC, HPLC(DAD), LC-MS, optical density etc.), biological assay methods (e.g., assaying activities of enzyme, such as acylase, demethylase, deaminase, etc.; assaying activities of biologically active substances, such as anti-bacterial, anti-fungal, anti-cancer activities, etc.), and so on. For example, the amount of actinorhodin is determined by measuring the optical density of supernatants at 633 nm.

When the multi-resistant microorganism is used, the step of selecting the strain having an increased productivity of the secondary metabolite can be carried out after obtaining the multi-resistant microorganism or after at least one step of introducing the mutation.

Using the recombinant DNA techniques, a strain having improved productivity of a secondary metabolite of interest can be obtained by transforming a host with a recombinant plasmid containing a gene for the biosynthesis of said secondary metabolite.

In the above-described steps, culturing of the microorganism can be carried out in accordance by utilizing a generally used culturing method.

The medium may be either a synthetic medium or a natural medium, as long as it contains appropriate amounts of necessary carbon sources, nitrogen sources, inorganic substances, amino acids, vitamins, and/or trace amounts of nutrient substances. They are shown in various papers, such as Hosoya, Y. et al, *Antimicrob. Agents Chemother*. (1998) 42:2041-2047; Kieser, T. et al, Practical *Streptomyces Genetics* (2000): 406-415; and Media information listed for bacteria in ATCC Media Handbook.

Examples of the carbon source include carbohydrates such as glucose, fructose, sucrose, maltose, mannose, glycerol, starch, starch hydrolysate and molasses, polyalcohols and various organic acids such as pyruvic acid, fumaric acid, lactic acid and acetic acid.

Examples of the nitrogen source include ammonia or various inorganic and organic ammonium salts such as ammonium chloride, ammonium sulfate, ammonium carbonate and ammonium acetate, urea and other nitrogen-containing substances, and nitrogen-containing organic substances such as peptone, NZ-amine, meat extract, yeast extract, corn steep liquor, casein hydrolysate and fish meal or a digested product thereof.

Examples of the inorganic substance include potassium dihydrogen phosphate, dipotassium hydrogen phosphate, ammonium sulfate, ammonium chloride, magnesium sulfate, sodium chloride, ferrous sulfate, manganese sulfate and calcium carbonate.

Amino acids and vitamins may be added to the medium as occasion demands.

The microorganism may be cultured under aerobic conditions such as shaking culture or aeration agitation culturing. In general, the culturing is carried out at a temperature of preferably from 20 to 40° C. It is desirable to maintain pH of the medium at around the neutral level. The culturing is carried out generally from a period of from 1 to 7 days.

The desired secondary metabolite formed and accumulated in the microorganism and/or culture medium can be recovered, for example, by the following method. The cells are removed after completion of the culturing, or the cells are disrupted and the resulting mixture is centrifuged to remove the disrupted cells. Then, the desired metabolite is recovered by a known method suitable for recovering the desired secondary metabolite, such as a concentration crystallization method, an activated carbon treatment method and/or an ion exchange resin method.

The present invention is further described taking *Streptomyces* strains as an illustrative example, but the present invention should not be construed as being limited thereto.

The strains belonging to the genus *Streptomyces* are explained below as the examples of the microorganism of the present invention, which can be divided into two groups: the wild type strain and drug-resistant mutants of *Streptomyces coelicolor* and non-identified *Streptomyces* sp. isolated from soils which normally do not produce antibiotics. Four kinds of antibiotics named as gentamicin, geneticin, streptomycin and rifampicin are explained below as the examples of the drug.

*Streptomyces coelicolor* is an excellent model strain to study antibiotic production and other process; it is the genetically more intensively studied *Streptomyces* species and produces four chemically different antibiotics, whose biosynthetic genes have been isolated: the blue-pigmented polyketide actinorhodin, undecylprodigiosin, methylenomycin and the calcium-dependent antibiotic. Among these, actinorhodin is a representative secondary metabolite and possesses a typical polyketide biosynthetic pathway. Characters of actinorhodin: fine red needles from dioxane, dec. 270° C. Absorption max (dioxane): 560, 523 nm. Soluble in piperidine, tetrahydrofuran, dioxane, phenol; slightly soluble in alcohol, acetic acid, acetone. Practically insol in aq acid; sol in aq alkali with bright blue color.

Characteristics of drugs:

Gentamicin:
Composition: this antibiotic complex consisting of three components: Gentamicin$C_1$, Gentamicin$C_2$ and Gentamicin$C_{1a}$. As shown in FIG. 10, they possess similar structures.
Action mechanism: act on ribosomal 16S RNA or other ribosomal proteins (L6 protein or other unknown proteins) resulting in inhibiting protein synthesis in ribosome.
Class: belonging to aminoglycoside antibiotics.

Geneticin:
Composition: single component and its structure as shown in FIG. 10.
Action mechanism: inhibiting protein synthesis by acting on 16S ribosomal RNA or unknown proteins.
Class: belonging to aminoglycoside antibiotics.

Streptomycin:
Composition: single component and structure as shown in FIG. 10, which exists large difference with those of gentamicin and geneticin.
Action mechanism: inhibiting protein synthesis by acting on ribosomal S12 protein and/or 16S RNA.
Class: belonging to aminoglycoside antibiotics.

Rifampicin:
Composition: single component and structure as shown in FIG. 10.
Action mechanism: inhibited RNA synthesis by acting on β-subunit of RNA polymerase.
Class: belonging to ansamycin antibiotics.

As an example of a preferred embodiment of this invention, actinorhodin productivity in *Streptomyces coelicolor* can be increased by introducing each antibiotic resistant mutations into the strain at a high frequency of 5-10% among streptomycin-resistant, gentamicin-resistant or rifampicin-resistant isolates. Most mutants are stable and able to grow and form aerial mycelia normally as well as wild type strain. Moreover, by introducing another antibiotic resistant mutation into single mutant, the actinorhodin productivity can be further enhanced 1.8-2.2 fold. Of course, the level of increase may differ among the mutants. Finally, the third mutation can be introduced into double mutants leading to triple mutants. Overproduction of actinorhodin in the triple mutants is then tested. These antibiotics possess different action positions so that their functions are additive and can be combined together for continuous improvement of antibiotic producers as shown in FIGS. 2, 4, 5 and 7. Mutational analyses showed that most rifampicin resistant mutants produced a point mutation within rpoB gene, encoding β-subunit of RNA polymerase, leading to high resistance levels to rifampicin; some streptomycin resistant mutants with high resistance level to streptomycin revealed a point mutation in rpsL gene encoding ribosomal S12 protein, but no mutation in this gene for low level resistant mutants; all gentamicin or geneticin resistant mutants showed no mutation in rpsL gene and their mutations maybe exist in an unknown gene. Although some mutational positions have not yet been determined, those mutations should exist in certain genes because the antibiotics used in this invention are known to act on the certain targets in ribosome.

Random mutagenesis and selection is referred to as the class of approach or non-recombinant strain improvement procedure. Improved mutants are normally identified by screening a large population of mutated organisms, since the mutant phenotype may not be easy to recognize, the desired mutations occur at an extremely low frequency. Although this approach has the advantage of being simple and reliable, random screening is time-consuming and costly.

Moreover, random mutation screening using mutagens possesses no certain targets and show a relatively large uncertainty. In contrast, method described in this invention use some antibiotics inhibiting protein or nucleic acid synthesis as screening agents, which are entirely distinguishable from traditional mutagens such as radiation rays, chemicals (base analogs, deaminating agents, alkylating agents or intercalating agents etc.) and biological agents (phage, plasmid or DNA transposons etc.). Moreover, the method described in this invention can produce high frequency of desired mutation so that selection of positive mutants do not need much time and labor.

Multi-drug resistant microorganisms which are obtained in the present invention can be used as heterogous hosts to express foreign genes encoding agriculturally and/or medically useful antibiotics, enzymes and biologically active substances, which are objective.

In addition to the manipulation of microorganisms by mutation, the techniques of genetic recombination provide another rational method for improving strains. It can be used to relieve rate-limiting steps of the biosynthetic pathway by increasing, for example, the gene dosage, or altering a regulation mechanism. Obviously this requires much knowledge of antibiotic production biochemistry and genetics like *Streptomyces coelicolor* and *E. coli*. However, most new antibiotic producers lack much knowledge so that this method is not applicable for most strains. Moreover, this method is costly and complex. In contrast, the method described in this invention does not require much knowledge of biochemistry and genetics of strains, and is simple and not costly. This new method can be used for the most microorganisms including *Streptomyces* or other bacteria, especially for the wild type strains isolated from nature.

Figure 9:
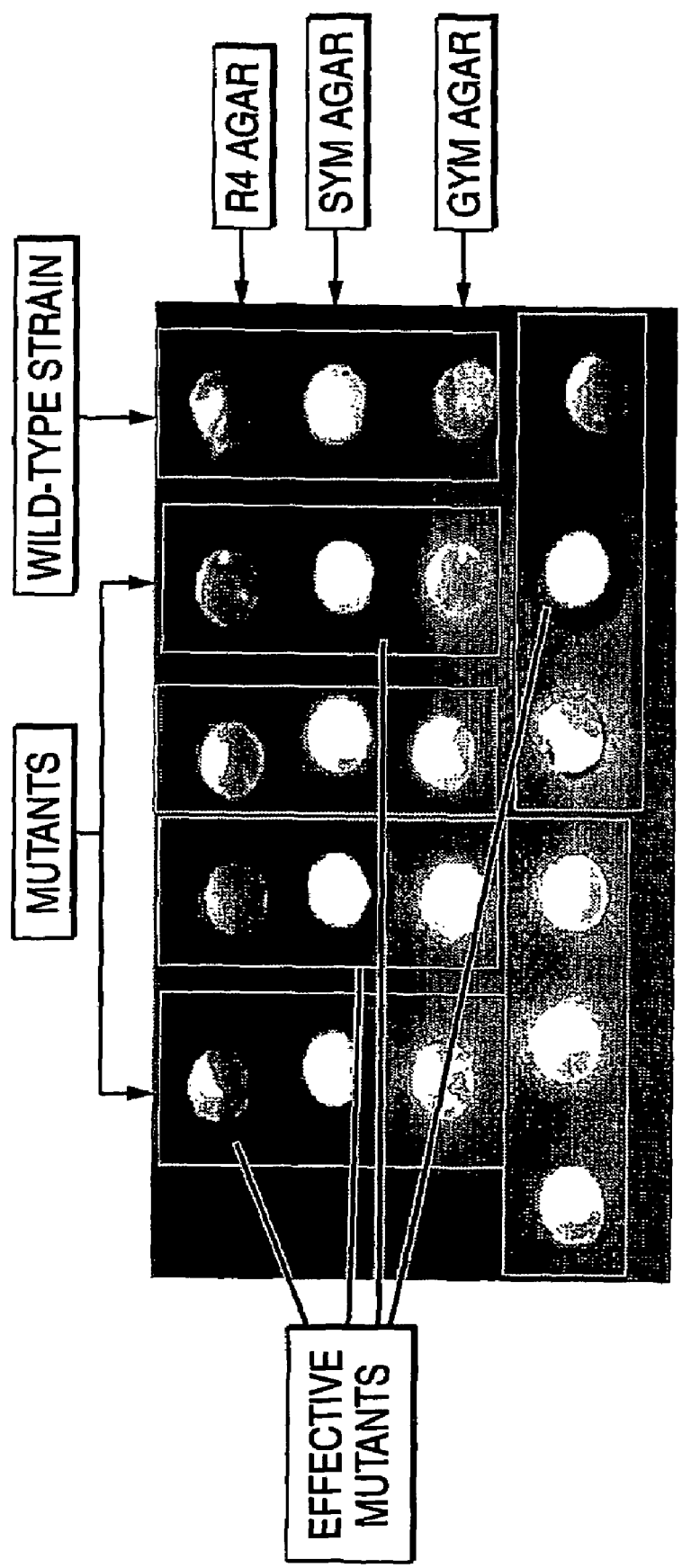
FIG. 9 is a photograph indicating the potentially new antibacterial agents produced in the mutants of certain Streptomyces strain No. 618824 by introducing drug-resistant mutations.

In addition to improving productivity of strains, the method described in this invention can be used to activate certain silent antibiotic biosynthetic genes by introducing drug-resistant mutations. The present inventors isolated a number of *Streptomyces* sp. from soils, which show no antibacterial activity and then selected the antibiotic resistant mutants with ability to produce antibacterial activity. The present inventors found that about 50% strains isolated from soils can be activated to produce antibiotics as shown in FIG. 9 and Table 3. Meanwhile, the antibiotic syntheses in mutants are medium-dependent as shown in FIG. 9. Therefore, it is important to use several different kinds of media to examine the productivity of antibacterial agents.

EXAMPLES

Examples of the preferred embodiments of the present invention will be described herein below. It should be understood that the present invention is not limited to these examples.

EXAMPLE 1

Spore stock of *Streptomyces coelicolor* wild type strain was spread on the GYM agar containing 0.4% of glucose, 0.4% of yeast extract, 1% of malt extract, 0.1% of peptone (NZ-Amine, Type A), 0.2% of NaCl and 2% of agar (before adding agar, adjust pH to 7.3). The medium was sterilized by an ordinary method (121° C., 15 min.). Then, the agar plates were incubated for 10-14 days at 30° C. to allow sporulation. The sterile distilled water (5 ml) was added to each plate and the surface scraped gently to release the spores. The suspensions were collected by centrifugation and washed twice with distilled water. Before use for inoculum, the spores were dispersed for 10 min. in a sonic bath. The concentrations of spores were adjusted to about $2 \times 10_u$ spores per ml.

The spontaneous streptomycin, gentamicin or rifampicin-resistant mutants of *S. coelicolor* were obtained as the colonies that grew within 7 days at 30° C. after spores (or cells) were spread on GYM agar (composition is the same as the above GYM agar) containing 5 µg streptomycin per ml or 1.0 µg of gentamicin per ml or 200 µg of rifampicin per ml, respectively (Growth of parental strain was inhibited completely with 1 µg of streptomycin per ml, 0.1 µg of gentamicin per ml or 10 µg of rifampicin per ml). The single colonies grew on screening plates were picked out and inoculated to R4 agar containing 1% of glucose, 0.1% of yeast extract, 0.001% of Casamino Acids, 0.3% of proline, 1% of $MgCl_2 \cdot 6H_2O$, 0.4% of $CaCl_2 \cdot 2H_2O$, 0.002% of $K_2SO_4$, 0.56% of TES [N-Tris (hydroxymethyl)methyl-2-aminoethanesulfonic acid], 0.2% of trace elements solution (as described for R2YE medium) and 2% of agar (before adding agar, adjusted to pH 7.2). The R4 plates were incubated at 30° C. for 6 days and the amount of blue pigment actinorhodin produced was compared among wild type strain and mutants, and selected the over-producers among the mutants. Then, the mutants with over-producing actinorhodin were inoculated into R4 liquid medium (composition is the same as the R4 agar, but no agar) in 25 ml of test tubes containing 5 ml medium on an orbital shaker at 30° C., 350 rpm. After incubation for 6 days, 1 ml culture samples were taken and adjusted pH to 8.0. After centrifugation at 1100 g for 5 min., actinorhodin production in supernatants was assayed by measurement of the optical density of supernatants at 633 nm. The highest productivity detected reached 1.6-fold for gentamicin-resistant mutants, 1.8-fold for streptomycin-resistant mutants and 3.0-fold for rifampicin-resistant mutants. The frequencies for such high producers were 5%, 6% and 10%, respectively (see Table 1 and FIG. 7).

Mutational analyses of the mutants were carried out by the procedure as described below. The rpsL gene fragment of the Str resistant mutant was obtained by PCR using a mutant genomic DNA as a template and synthetic oligonucleotide primers P1 (forward: 5'-ATTCGGCACACA-GAAAC) (SEQ ID NO:1) and P2 (reverse: 5'-AGAG-GAGAACCGTAGAC) (SEQ ID NO:2) designed on the basis of sequence of *S. lividans* (DDBJ accession no: D83746). PCR was performed by following the manufacturer's instructions and using Taq polymerase (Takara Ex Taq). A Perkin-Elmer Cetus thermal cycler was used, and conditions were 5 min. of incubation at 96° C., followed by 30 cycles of 96° C. for 0.3 min., 55° C. for 0.2 min. and 72° C. for 0.5 min., finally at 72° C. for 10 min. PCR products were directly sequenced by the dideoxy chain-termination procedure using the Bigdye Terminator Cycle Sequencing kit(Perkin-Elmer Applied Biosystems, Foster City, Calif., U.S.A). The sequence data were analyzed with the GENETIX program (Software Development Co., Tokyo, Japan).

The partial rpoB gene fragment of the Rif resistant mutant was obtained by PCR using a mutant genomic DNA as a template and synthetic oligonucleotide primers P3 (forward: 5'-GGCCGCTACAAGGTGAACAAGAAG) (SEQ ID NO:3) and P4 (reverse: 5'-CGATGACGAAGCGGTC-CTCC) (SEQ ID NO:4) designed on the basis of sequence of *S. coelicolor* M145. The PCR method and DNA sequencing are the same as those in rpsL gene. The rpsL genes of 3 gentamicin-resistant mutants and 3 streptomycin-resistant mutants were sequenced and compared to that of *Streptomyces coelicolor* wild type strain. The partial rpoB genes of 3 rifampicin-resistant mutants were sequenced and compared to that of *Streptomyces coelicolor* wild type strain. Three rifampicin-resistant mutants exhibited a point mutation in this region of rpoB gene; only one streptomycin-resistant mutant possessed a point mutation within rpsL gene; All gentamicin-resistant mutants showed no mutation in rpsL gene (see Table 2).

EXAMPLE 2

The spore solution of strain S-1 (a streptomycin-resistant mutant) was prepared by the same procedure as used in Example 1.

The spontaneous geneticin, gentamicin or rifampicin-resistant mutants of S-1 were obtained as colonies that grew on GYM agar containing 2.5 µg of geneticin per ml or 2.5 µg of gentamicin per ml or 200 µg of rifampicin per ml. (Growth of S-1 strain was inhibited completely with 0.5 µg of geneticin per ml, 0.5 µg of gentamicin per ml or 10 µg of rifampicin per ml.). Actinorhodin productivity of mutants was examined using R4 agar plates and R4 liquid medium.

The highest productivity detected reached 1.7-fold for geneticin-resistant mutants, 2.2-fold for gentamicin-resistant mutants and 2.5-fold for rifampicin-resistant mutants. The frequencies of these high producers were 13%, 14% and 18%, respectively (see Table 1 and FIG. 7). Mutational analyses of the mutants were carried out by the procedure as described in Example 1. All three antibiotic resistant mutants obtained here kept the mutation in rpsL gene from S-1, but no additional mutation was found in rpsL gene. Seven rifampicin-resistant mutants produced a point mutation in rpoB gene (see Table 2).

EXAMPLE 3

The spore solutions of SG-1 and SG-2 strains (gentamicin- and streptomycin-resistant double mutants) were prepared by the same procedure as used in Example 1.

The spontaneous rifampicin-resistant mutants of SG-1 and SG-2 strains were obtained as colonies that grew on GYM agar containing 200 μg of rifampicin per ml. (Growth of SG-1 and SG-2 strains were completely inhibited with 10 μg of rifampicin per ml.) for 7 days at 30° C.

Actinorhodin productivity of mutants was examined using R4 agar plates and R4 liquid medium.

The highest productivity detected reached 3.4-fold for rifampicin-resistant mutants of SG-1 strain and 3.6-fold for rifampicin-resistant mutants of SG-2 strain. The frequencies of such high producers were 10% and 15%, respectively (see Table 1 and FIG. 7). Mutational analyses were carried out by the procedure as described in Example 1. Five rifampicin-resistant mutants were found to have a point mutation in rpoB gene, but one mutant had no mutation in this region (see Table 2).

TABLE 1

Screening and antibiotic productivity of drug-resistant mutants

| Strain | Actinorhodin productivity ($OD_{633}$)[a] | MIC (μg/ml)[b] | Concn. of antibiotic used for screening (μg/ml) | Frequency(%) of mutants producing increased actinorhodin[c] | Highest productivity detected ($OD_{633}$)[d] |
|---|---|---|---|---|---|
| S. coelicolor 1147 (wild type) | 0.77 | Gentamicin (0.1) | 1.0 | 5 (4/80) | 1.25 |
| | | Streptomycin(1.0) | 5 | 6 (7/120) | 1.39 |
| | | Rifampicin(10) | 200 | 10 (15/150) | 2.32 |
| S-1 | 1.28 | Geneticin (0.2) | 2.5 | 13 (15/112) | 2.22 |
| | | Gentamicin(0.1) | 2.5 | 14 (14/104) | 2.80 |
| | | Rifampicin(10) | 200 | 18 (21/116) | 3.14 |
| SG-1 | 2.02 | Rifampicin(10) | 200 | 10 (8/80) | 6.88 |
| SG-2 | 1.88 | Rifampicin(10) | 200 | 15 (12/80) | 6.68 |

[a-d]OD of supernatant was determined at 633 nm after 6 days of cultivation at 30° C., using 25 ml test tube containing 5 ml of R4 medium. All measurements were done in triplicate and the mean value was presented.
[b]Determined after 2 days of incubation on GYM agar.
[c]Mutants producing more antibiotic than starting strain. Numbers in parentheses are number of mutants producing more antibiotic/number of mutants tested.

TABLE 2

Summary of mutations on the S. coelicolor rpsL or rpoB gene resulting in amino acid exchange

| Strain | Position in rpsL gene[a] | Amino acid position (exchange) | Position in rpoB gene[b] | Amino acid position (exchange) | STR[d] | GEN | RIF | GNE |
|---|---|---|---|---|---|---|---|---|
| 1147 | —[e] | | | | 1 | 0.1 | 10 | 0.2 |
| S-1 | 262A→G | 88(Lys→Glu) | | | 100 | | | |
| S-2 | ND[f] | | | | 5 | | | |
| S-3 | ND | | | | 10 | | | |
| G-1 | ND | | | | | 0.3 | | |
| G-2 | ND | | | | | 0.3 | | |
| G-3 | ND | | | | | 0.3 | | |
| R-1 | | | 1049G→A | 350(Arg→His) | | | 400 | |
| R-2 | | | 1040A→G | 347(His→Arg) | | | 400 | |
| R-3 | | | 1049G→T | 350(Arg→Phe) | | | 400 | |
| SGe-1 | 262A→G | 88(Lys→Glu) | | | 100 | | | 0.5 |
| SGe-2 | 262A→G | | | | 100 | | | 1 |
| SGe-3 | 262A→G | | | | 100 | | | 1 |
| SG-1 | 262A→G | | | | 100 | 0.3 | | |
| SG-2 | 262A→G | | | | 100 | 0.3 | | |
| SG-3 | 262A→G | | | | 100 | 0.3 | | |
| SR-1 | 262A→G | | 995T→C | 332(Leu→Arg) | 50 | | 50 | |
| SR-2 | 262A→G | | 1154C→T | 385(Pro→Leu) | 50 | | 150 | |
| SR-3 | 262A→G | | 1179C→G | 393(Ile→Met) | 50 | | 400 | |
| SR-4 | 262A→G | | 1011C→A | 337(Asp→Glu) | 100 | | 400 | |
| SR-5 | 262A→G | | 1010A→G | 337(Asp→Gly) | 100 | | 400 | |
| SR-6 | 262A→G | | 1028C→T | 343(Ser→Leu) | 50 | | 400 | |
| SR-7 | 262A→G | | 1048C→T | 350(Arg→Cys) | 50 | | 400 | |
| SGR-1 | 262A→G | | 1039C→T | 347(His→Tyr) | 100 | 0.2 | 400 | |
| SGR-2 | 262A→G | | 1041C→A | 347(His→Gln) | 100 | 0.2 | 400 | |

TABLE 2-continued

Summary of mutations on the S. coelicolor rpsL or rpoB gene resulting in amino acid exchange

| Strain | Position in rpsL gene[a] | Amino acid position (exchange) | Position in rpoB gene[b] | Amino acid position (exchange) | Resistance level (µg/ml)[c] to: | | | |
|---|---|---|---|---|---|---|---|---|
| | | | | | STR[d] | GEN | RIF | GNE |
| SGR-3 | 262A→G | | ND | | 50 | 0.3 | 300 | |
| SGR-4 | 262A→G | | 1039C→T | 347(His→Tyr) | 50 | 0.2 | 400 | |
| SGR-5 | 262A→G | | 1054A→T | 352(Asn→Tyr) | 50 | 0.5 | 400 | |
| SGR-6 | 262A→G | | 1027C→T | 343(Ser→Pro) | 100 | 0.3 | 300 | |

[a,b]Numbering originates from the start codon (GTG or ATG) of the open reading frame.
[c]Determined after 4 days of cultivation on GYM agar.
[d]STR, GEN, RIF and GNE represent streptomycin, gentamicin, rifampicin and geneticin, respectively.
[e]—, wild-type rpsL gene.
[f]Mutations were not detected within the rpsL or rpoB gene.

EXAMPLE 4

Figure 5:
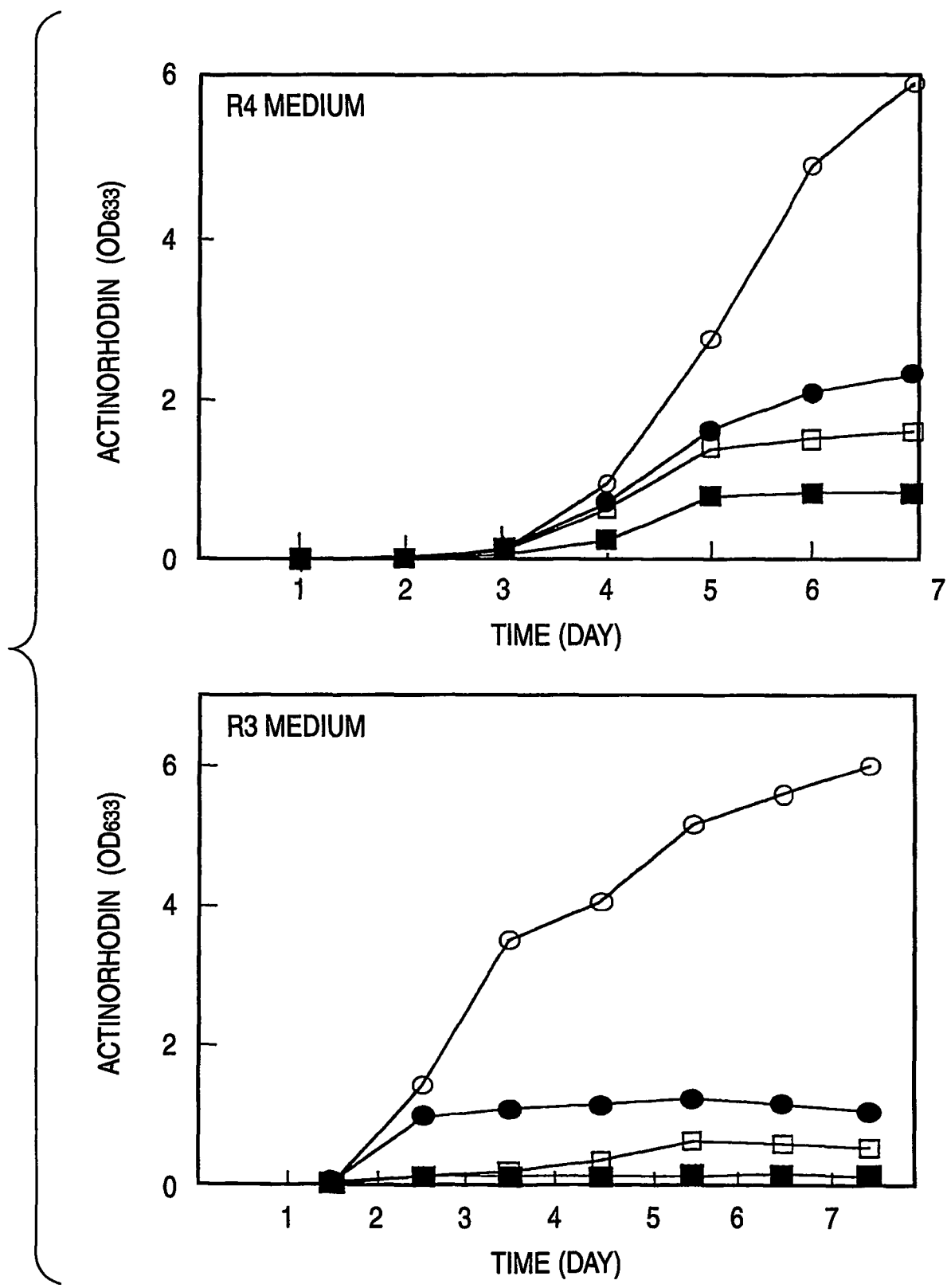
FIG. 5 is a graph indicating actinorhodin production in media R4 and R3. Symbols: ■, 1147 (wild type); □, S-1 (str); ●, SG-1 (str-gen); ○, SGR-1 (str-gen-rif).

The time courses of actinorhodin biosynthesis were carried out by using Streptomyces coelicolor wild type strain, S-1 (a streptomycin-resistant mutant), SG-1 (a gentamicin and streptomycin resistant double mutant) and SGR-1 (a genetamicin-, streptomycin- and rifampicin-resistant triple mutant). Erlenmeyer flask of 500 ml-capacity containing 150 ml of R4 or R3 medium was inoculated with spore solutions, then incubated at 30° C. on an orbital shaker at 200 rpm for the denoted time. The composition of R4 liquid medium was the same as used in Example 1. The R3 liquid medium was the same as R4 but contained an increased amount (0.5%) of yeast extract and an extra $KH_2PO_4$ (0.005%). At 24 h, 48 h, 72 h, 96 h, 120 h, 144 h or 168 h of incubation for R4 medium (at 36 h, 60 h, 84 h, 108 h, 132 h, 156 h, 180 h of incubation for R3 medium), 1 ml culture samples were taken and adjusted pH to 8.0. After centrifugation at 1100 g for 5 min., actinorhodin production was assayed by measurement of the optical density of supernatants at 633 nm. The results as shown in FIG. 5, these single, double and triple mutants displayed in hierarchical order a remarkable increase in the actinorhodin biosyntheses.

EXAMPLE 5

Figure 6:
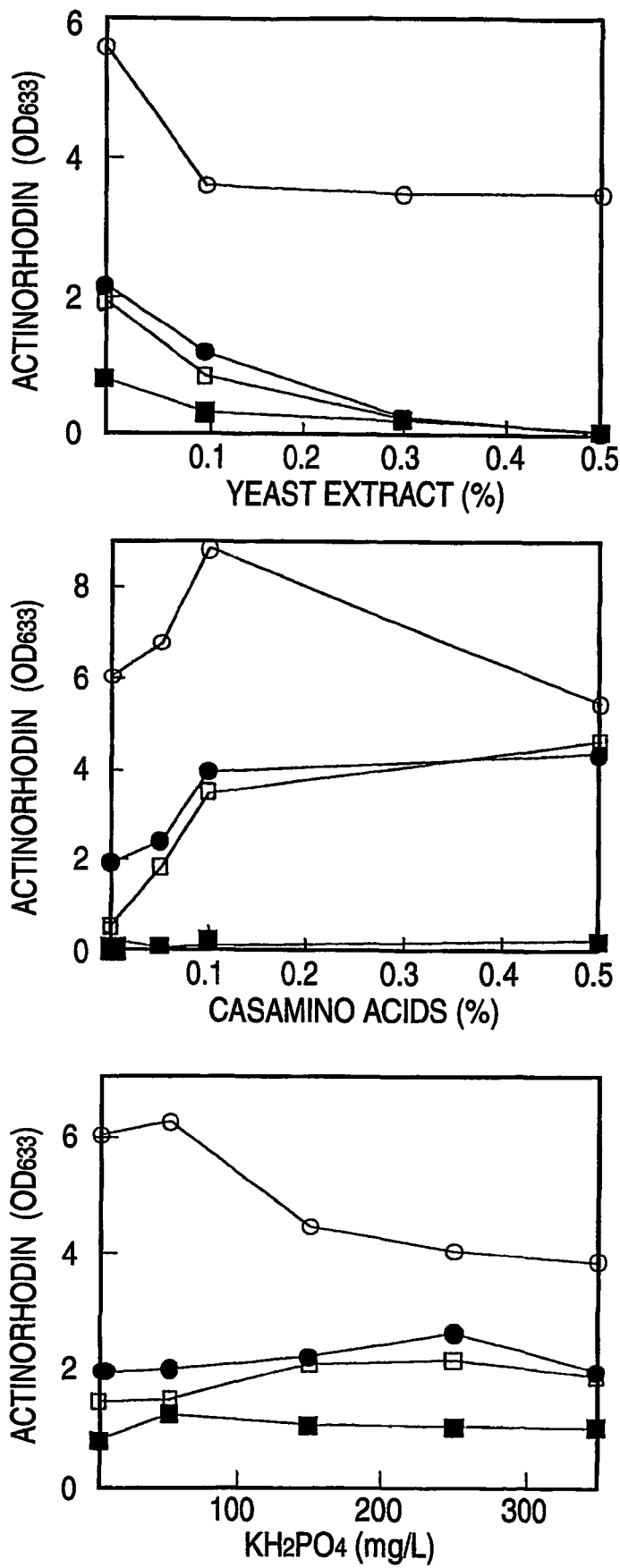
FIG. 6 is a graph indicating the effect of yeast extract, Casamino acids and $KH_2PO_4$ on the production of actinorhodin. Strains were grown for 6 days in R4 medium supplemented with various concentrations of yeast extract, Casamino acids or $KH_2PO_4$. Symbols: ■, 1147 (wild type); □, S-1 (str); ●, SG-1 (str-gen); ○, SGR-1 (str-gen-rif).
Figure 7:
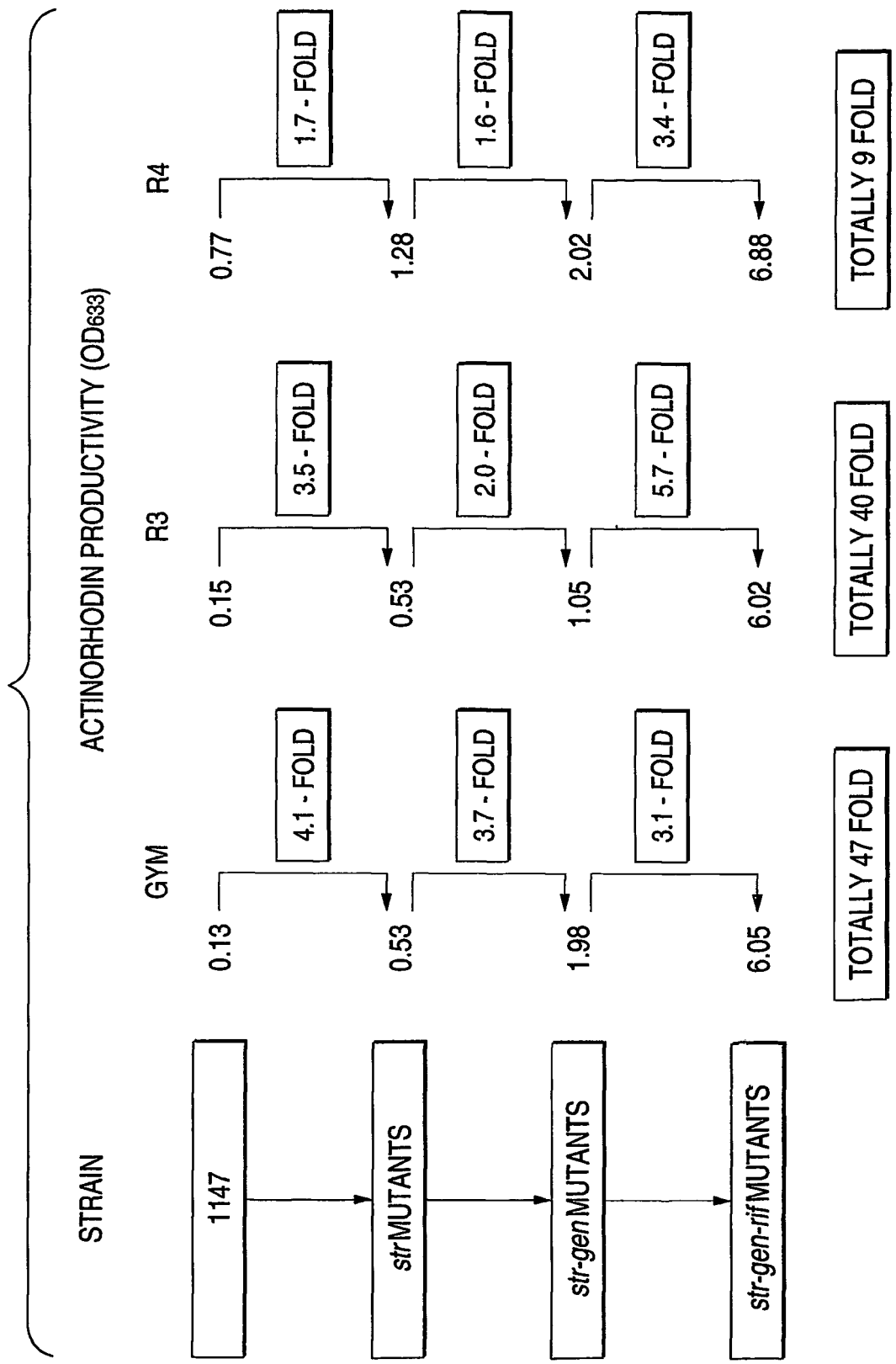
FIG. 7 is a graph indicating increased productivity of actinorhodin in combined resistant mutants. Cultures were grown for 7 days in GYM, R3 or R4 liquid medium. The strains S-1, SG-1 and SGR-1 were used as single, double and triple mutants, respectively.
Figure 8:
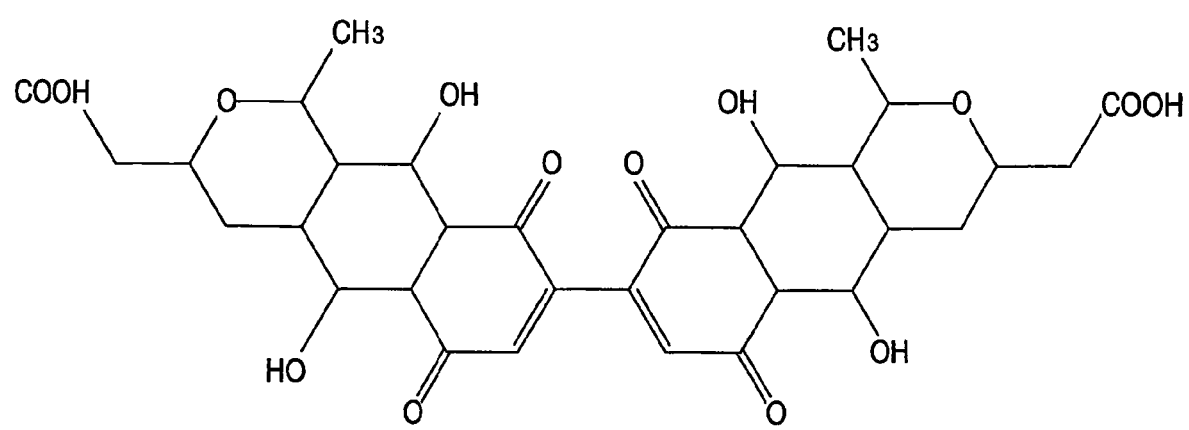
FIG. 8 is a graph indicating the chemical structure of actinorhodin produced by Streptomyces coelicolor.

The effects of nutritional source on actinorhodin production were investigated by using the strains and procedures as described in Example 4. R4 liquid medium, was used as the basic medium, which was supplemented with different amounts of yeast extract, Casamino acids or $KH_2PO_4$, respectively. Actinorhodin assay was the same as described in Example 4. As shown in FIG. 6, supplementation of yeast extract resulted in the severe impairment of actinorhodin productivity. This result was less pronounced in the triple mutant. Unlike yeast extract, Casamino acids was effective for enhancing actinorhodin production in the single, double or triple mutants but not the wild type strain, demonstrating the efficacy of those drug-resistant mutations. $KH_2PO_4$ had virtually no effect on actinorhodin productivity.

EXAMPLE 6

The unidentified Streptomyces isolated from soils were inoculated to GYM agar for preparing spore solutions as described in Example 1. The screening of streptomycin, gentamicin or rifampicin resistant mutants was as described in Example 2. The resistant mutants were inoculated to GYM agar, R4 agar and SYM agar, and incubated at 30° C. for 6 days. The composition of GYM agar and R4 agar was the same as described in Example 1. SYM agar contained 1% of soluble starch, 0.2% of yeast extract, 0.5% of glucose and 2% agar (before adding agar, adjust pH to 7.3).

The agar plug method was used to detect productivity of an antibiotic in mutants by measuring the extent of growth inhibition (diameters of inhibitory zones) of test organisms (E. coli K12, S. aureus 209P, B. subtilis 6633 or Candida albicans).

The results of screening are shown in FIG. 9 and Table 3.

TABLE 3

Results of screening for the strains from No. 101 to 200

| | |
|---|---|
| Starting date: Feb. 06, 2000 | Finishing date: May 09, 2000 |
| Number of strains tested | 100 |
| | No. 618749 to No. 618892 |
| Number of strains producing drug-resistant mutants | 95 |
| Number of strains producing mutants that produce antibiotics | 45 |
| Number of strains producing the mutants to act on E. coli K12 | 6 |
| Number of strains producing the mutants to act on C. albicans | 17 |
| Number of strains producing the mutants to act on S. aureus 209P | 38 |
| Number of strains producing the mutants to act on B. subtilis 6633 | 39 |

EXAMPLE 7

A gentamicin-resistant mutant and a rifampicin-and gentamicin-resistant mutant of Bacillus cereus No. 2045 were produced according to a similar manner to that of Examples 1, 2 or 3. Those mutants were precultured in bouillon medium for 10 h. Cells (0.1 ml) were inoculated into 5 ml of production medium consisting of (per liter) 20 g of polypeptone, 20 g of corn steep liquor, and 5 g of NaCl (adjusted to pH 7.5 with NaOH) for 2 days at 30° C. The results are shown in Table 4.

TABLE 4

| Screening results and characteristics of mutants | | | | |
|---|---|---|---|---|
| Strain | Genotype | Resistance level to GEN*[2] (μg/ml) | Resistance level to RIF*[2] (μg/ml) | Productivity*[4] (μg/ml) of WB2045*[3] |
| *B. cereus* No. 2045 | Wild-type | 0.8 | 1.0 | 60 |
| BG-1 | gen*[1] | 4.0 | 1.0 | 126 |
| BG-2 | gen | 4.0 | 0.8 | 135 |
| BG-3 | gen | 4.5 | 1.0 | 130 |
| BGR-1 | gen-rif | 4.5 | 100 | 380 |
| BGR-2 | gen-rif | 5.0 | 120 | 340 |
| BGR-3 | gen-rif | 5.0 | 150 | 285 |

*[1]gen indicates resistant to gentamicin, gen-rif indicates resistant to gentamicin and rifampicin.
*[2]GEN indicates gentamicin and RIF indicates rifampicin.
*[3]WB2045 is a substance having an anti-microbial activity, which is produced by *Bacillus cereus* No. 2045 (=FERM BP-1791) (USP4, 950, 605).
*[4]Antibacterial activity of WB2045 against *Bacillus subtilis* 6633 strains was determined by a conventional paper disc diffusion assay (Toyo Roshi; thick type 9 mmΦ) on agar plate using 1.7 × NG medium [a medium developed for antibiotic production by *Bacillus subtilis*, contained (per liter) 17 g of nutrient broth (Difco), 17 g of glucose, 3.4 g of NaCl, 8.5 mg of $CuSO_4•5H_2O$, 12.75 mg of $FeSO_4•7H_2O$, 6.12 mg of $MnSO_4•5H_2O$, 25.5 mg of $CaCl_2•2H_2O$, and 15.3 mg of $ZnSO_4•7H_2O$ (adjusted to pH 7.2 with NaOH)] for 48 hr at 30° C.

EXAMPLE 8

A rifampicin-resistant mutant and a streptomycin-and rifampicin-resistant mutant of *Streptomyces lividans* 66 were produced according to a similar manner to that of Examples 1, 2 or 3, and the actinorhodin production was estimated. The results are shown in Table 5.

TABLE 5

| Screening results and characteristics of mutants | | | | |
|---|---|---|---|---|
| strain | genotype | Resistance level to RIF (μg/ml)*[1] | Resistance level to STR (μg/ml)*[1] | Productivity of Act ($OD_{633}$ nm)*[2] |
| *S. lividans* 66 | Wild-type | 10 | 1.0 | 0.089 |
| SR-1 | rif[1] | 200 | 1.0 | 0.265 |
| SR-2 | rif | 400 | 0.8 | 0.864 |
| SR-3 | rif | 400 | 1.0 | 0.684 |
| SRS-1 | rif-str | 400 | 50 | 1.200 |
| SRS-2 | rif-str | 350 | 120 | 1.801 |
| SRS-3 | rif-str | 400 | 100 | 1.342 |

*[1]rif or rif-str, resistant to rifampicin or resistant to rifampicin and streptomycin; RIF, rifampicin; STR, streptomycin.
*[2]Actinorhodin (Act) production was determined by assaying the OD values at 633 nm of supernatants of liquid cultures in R4 medium after cultivating 5 days at 30° C.

While the invention has been described in detail and with reference to specific embodiments thereof, it will be apparent to one skilled in the art that various changes and modifications can be made therein without departing from the spirit and scope thereof.

This application is based on U.S. Provisional Patent Application No. 60/279,665 filed Mar. 30, 2001, the entire contents thereof being hereby incorporated by reference.

INDUSTRIAL APPLICABILITY

The present invention provides a method for increasing the productivity of the secondary metabolite by a microorganism in a labor-saving, time-saving, high efficient and semi-rational way and being applicable for the strains without more knowledge of, for example, antibiotic biochemistry and genetics.

The invention claimed is:

1. A method for obtaining a microorganism having an increased productivity of a secondary metabolite, which comprises:
conferring antibiotic resistance on a microorganism by culturing an original microorganism in a medium containing at least two antibiotics, wherein the concentration of each of said antibiotics is higher than MIC (minimum inhibitory concentration) of each of said antibiotics against the original microorganism, and
isolating an antibiotic-resistant microorganism which can grow in said medium;
wherein said isolated antibiotic-resistant microorganism contains a mutation in an rpsL gene conferring antibiotic resistance,
contains a mutation in gene other than an rpsL gene which confers antibiotic resistance,
and produces a higher amount of a secondary metabolite than the original microorganism.

2. The method of claim 1, wherein said microorganism is a bacterium.

3. The method of claim 1, wherein said microorganism is selected from the group consisting of Streptomyces, Bacillus and Pseudomonas.

4. The method of claim 1, wherein said microorganism is selected from the group consisting of Streptomyces coelicolor, Streptomyces lividans, Streptomyces antibioticus, and Streptomyces chattanoogenis.

5. The method of claim 1, wherein said microorganism is selected from the group consisting of Bacillus subtilis and Bacillus cereus.

6. The method of claim 1, wherein said microorganism is Pseudomonas pyrrocinia.

7. The method of claim 1, wherein said antibiotic-resistance based on mutation in an rpsL gene is streptomycin-resistance.

8. The method of claim 1, wherein said antibiotic-resistance based on mutation in gene other than an rpsL gene is resistance to antibiotic selected from the group consisting of ribosomal protein-attacking antibiotic, ribosomal RNA-attacking antibiotic and RNA polymerase-attacking antibiotic.

9. The method of claim 1, wherein said antibiotic-resistance based on mutation in gene other than an rpsL gene is resistance to antibiotic selected from the group consisting of genticin, gentamicin and rifampicin.

10. The method of claim 1, wherein said antibiotic-resistance based on mutation in a gene other than an rpsL gene is antibiotic-resistance based on mutation in rpoB gene.

11. The method of claim 8, wherein said antibiotic-resistance based on mutation in an rpoB gene is rifampicin-resistance.

12. The method of claim 1, wherein said secondary metabolite is at least one antibiotic.

13. The method of claim 1, wherein said secondary metabolite is at least one enzyme.

14. The method of claim 1, wherein said secondary metabolite is at least one physiologically active substance which is not an antibiotic or enzyme.

15. A method for producing at least one secondary metabolite comprising:
culturing a mutated microorganism which produces a higher amount of at least one secondary metabolite compared to an unmutated parent strain, wherein said mutated microorganism is obtained by:
mutating the parent strain by culturing it in a medium containing at least two antibiotics which are at a concentration above their MIC (minimal inhibitory concentration) for the parent strain, and selecting a mutated microorganism which produces a higher amount of a secondary metabolite compared to the parent strain;
wherein said mutated has an antibiotic-resistance based on a mutation in the rpsL gene of the parent strain and an antibiotic-resistance based on a mutation in a gene of the parent strain other than the rpsL gene.

16. The method of claim 15, wherein said mutated microorganism is an *Actinomycete* which contains a mutation in the rpsL gene that confers resistance to streptomycin compared to a parent microorganism not containing said rpsL mutation, and which contains a mutation in a non-rpsL gene conferring resistance to rifampicin, geneticin or gentamycin compared to the parent microorganism not containing said non-rpsL mutation.

17. The method of claim 15, wherein said mutated microorganism is *Steptomyces* which produces the secondary metabolite actinorhodin, or *Bacillus* which produces the secondary metabolite WB2045, at a level higher than that produced by the unmutated parent strain.

* * * * *